US009155751B2

(12) United States Patent
Suzuki et al.

(10) Patent No.: US 9,155,751 B2
(45) Date of Patent: Oct. 13, 2015

(54) SOLUTION FOR TISSUE ADHESION PREVENTION AND METHOD FOR TISSUE ADHESION PREVENTION

(75) Inventors: Shigeki Suzuki, Tokyo (JP); Yoshikatsu Miwa, Okayama (JP); Nobuo Sasaki, Tokyo (JP); Yuiichi Tei, Tokyo (JP)

(73) Assignees: THE UNIVERSITY OF TOKYO, Tokyo (JP); KABUSHIKI KAISHA HAYASHIBARA SEIBUTSU KAGAKU KENKYUJO, Okayama (JP); OTSUKA PHARMACEUTICAL FACTORY, INC., Tokushima (JP)

( * ) Notice: Subject to any disclaimer, the term of this patent is extended or adjusted under 35 U.S.C. 154(b) by 28 days.

(21) Appl. No.: 13/047,551

(22) Filed: Mar. 14, 2011

(65) Prior Publication Data

US 2011/0166089 A1     Jul. 7, 2011

Related U.S. Application Data

(62) Division of application No. 11/917,026, filed as application No. PCT/JP2006/311501 on Jun. 8, 2006, now abandoned.

(30) Foreign Application Priority Data

Jun. 8, 2005 (JP) .................................. 2005-168744

(51) Int. Cl.
*A61K 31/7016* (2006.01)
*A61P 41/00* (2006.01)
(Continued)

(52) U.S. Cl.
CPC ........... *A61K 31/7016* (2013.01); *A61L 31/042* (2013.01)

(58) Field of Classification Search
None
See application file for complete search history.

(56) References Cited

U.S. PATENT DOCUMENTS 4,994,277 A    2/1991   Higham et al.
5,827,640 A   10/1998   Wiggins et al.
(Continued)

FOREIGN PATENT DOCUMENTS

CA    2416754    6/2001
EP    1018866    7/2000
(Continued)

OTHER PUBLICATIONS

Adult Reconstructive Orthopaedics (retrieved on Nov. 19, 2014 from https://www.aamc.org/cim/specialty/list/us/341646/adult_reconstructive_orthopaedics_-orthopaedic_surgery.html).*

(Continued)

*Primary Examiner* — Ernst V Arnold
*Assistant Examiner* — Jianfeng Song
(74) *Attorney, Agent, or Firm* — Greenblum & Bernstein, P.L.C.

(57) ABSTRACT

The objective of the invention is to provide a solution for tissue adhesion prevention and a method for tissue adhesion prevention that are applicable to general surgery and in which covering condition during surgery is stable and convenient. The invention is the solution for tissue adhesion prevention of which the active ingredient is trehalose. Also, it contains at least one or more among antioxidants, chelates, antiseptics, hemostatics, anti-inflammatory agents, and polysaccharides, mucopolysaccharides, salts of polysaccharides and salts of mucopolysaccharides having lubricating properties. This solution for tissue adhesion prevention is provided as any form of perfusion fluid, spray fluid, solution for spray or vaporization administration, foam-like aerosol preparation, injection solution for intravenous fluids, intravenous fluid.

21 Claims, 2 Drawing Sheets

(51) Int. Cl.
  *A61K 31/7048* (2006.01)
  *A61P 39/06* (2006.01)
  *A61L 31/04* (2006.01)

(56) References Cited

U.S. PATENT DOCUMENTS

| | | | |
|---|---|---|---|
| 6,020,367 | A | 2/2000 | Duffy et al. |
| 6,365,338 | B1 | 4/2002 | Bull et al. |
| 6,653,062 | B1 * | 11/2003 | DePablo et al. ............ 435/1.2 |
| 7,427,607 | B2 | 9/2008 | Suzuki |
| 2004/0047892 | A1 * | 3/2004 | Desrosiers et al. ........... 424/423 |
| 2009/0098061 | A1 * | 4/2009 | Suzuki et al. ................ 424/45 |

FOREIGN PATENT DOCUMENTS

| | | |
|---|---|---|
| EP | 1 512 404 | 3/2005 |
| EP | 1 745 747 | 1/2007 |
| JP | 6-40801 | 2/1994 |
| JP | 6-72883 | 3/1994 |
| JP | 6-256219 | 9/1994 |
| JP | 6-319486 | 11/1994 |
| JP | 9-235233 | 9/1997 |
| JP | 09-278610 | 10/1997 |
| JP | 2948254 | 9/1999 |
| JP | 2000-512625 | 9/2000 |
| JP | 2002-24832 | 1/2002 |
| JP | 2003-089601 | 3/2003 |
| JP | 3420851 | 6/2003 |
| JP | 2004-224677 | 8/2004 |
| JP | 2006-188672 | 7/2006 |
| WO | 93/15234 | 8/1993 |
| WO | 97/47192 | 12/1997 |
| WO | 00/07634 | 2/2000 |
| WO | 00/64254 | 11/2000 |
| WO | 00/72872 | 12/2000 |
| WO | 2004/071472 | 8/2004 |
| WO | 2004/076602 | 9/2004 |
| WO | 2004/098285 | 11/2004 |
| WO | 2004/106549 | 12/2004 |
| WO | 2004/107883 | 12/2004 |
| WO | 2005/030248 | 4/2005 |
| WO | 2006/026170 | 3/2006 |
| WO | WO 2006132310 A1 * | 12/2006 |

OTHER PUBLICATIONS

International Search Report and Written Opinion dated Sep. 12, 2006, from the Japanese Patent Office in related Japanese PCT Application No. PCT/JP2006/311501 (2 pages).
Extended European Search Report and Written Opinion dated Nov. 16, 2009, from the European Patent Office in related European Patent Application No. EP-06766477.1 (8 pages) [Previously submitted in Parent U.S. Patent U.S. Appl. No. 11/917,026.].
Database WPI Week 200349, Thomson Scientific, London, GB; AN 2003-517056; XP002554237 [See: JP2003-089601].
Database WPI Week 199802, Thomson Scientific, London, GB; AN 1998-014641; XP002554238 [ See: JP09-278610].
EPO Office Action dated Dec. 3, 2009, from the European Patent Office in related European Patent Application No. 06766477.1 (1 page).
EPO Office Action dated Feb. 17, 2010. from the European Patent Office in related European Patent Application No. 06766477.1 (2 pages).
EPO Office Action (intent to grant patent) dated May 10, 2010, from the European Patent Office in related European Patent Application No. 06766477.1 (4 pages).
EPO Decision to Grant a European Patent dated Nov. 18, 2010, from the European Patent Office in related European Patent Application No. 06766477.1 (3 pages).
Office Action dated Jan. 13, 2011, from the U.S. Patent and Trademark Office in related U.S. Appl. No. 11/917,026 (2 pages).
G.S. Dizerega et al., "A randomized, controlled pilot study of the safety and efficacy of 4% icodextrin solution in the reduction of adhesions following laparoscopic gynaecological surgery", Human Reproduction, vol. 17, No. 4, European Society of Human Reproduction and Embryology., 2002, pp. 1031-1038.
"JP1998-014641A" Bausch & Lomb, Abstract , Published Oct. 20, 1998.
S.J.S. Verco et al., "Development of a novel glucose polymer solution (icodextrin) for adhesion prevention: pre-clinical studies. "Human Reproduction, vol. 15, No. 8, European Society of Human Reproduction and Embryology., 2000, pp. 1764-1772.
Fengshi Chen et al., "Development of New Organ Preservation Solution in Kyoto University", Yonsei Medical Journal, vol. 45 No. 6 , 2004, pp. 1107-1114.
Hirata Toshiki et al., "Effects of trehalose in canine lung preservation ", Surgery, vol. 115 , 1994, pp. 102-107.
"JP2003-517056A", Menicon Co., Ltd., Abstract, Published Mar. 28, 2003.
Vietnamese Office Action as issued in Vietnamese Patent Application No. 1-2008-00035, mail date is Dec. 14, 2009.
Malaysian Office Action as issued in Malaysian Patent Application No. 20062635, mail date is Oct. 30, 2009.
Official Action in Russian Application No. 2007149561/15(054370), mail date is Apr. 14, 2009.
Australian Office Action as issued in Australian Patent Application No. 2006256084, mail date is Jun. 10, 2009.
Canadian Office Action as issued in Canadian Patent Application No. 2,611,441, mail date is Oct. 22, 2009.
Office Action Issue in New Zealand Patent Application. No. 564399, mail date is Sep. 26, 2009.

* cited by examiner

SOLUTION FOR TISSUE ADHESION PREVENTION AND METHOD FOR TISSUE ADHESION PREVENTION

CROSS REFERENCE TO RELATED APPLICATIONS

This Application is a Division of U.S. patent application Ser. No. 11/917,026, filed on Dec. 10, 2007 and claims benefit under 35 U.S.C. §120 of PCT/JP2006/311501, filed on Jun. 8, 2006, which claims benefit of Japanese patent application JP 2005-168744, filed on Jun. 8, 2005. This application claims benefits of all these prior applications and incorporate these prior applications by reference in their entirety.

FIELD OF THE INVENTION

This invention relates to a solution for tissue adhesion prevention and a method for tissue adhesion prevention, especially to the solution for tissue adhesion prevention and the method for tissue adhesion prevention composed of trehalose, and that prevents dehydration and oxidation upon exposure to air associated with surgery, and that can prevent complications such as tissue adhesion including postoperative organs.

BACKGROUND ART

It is well known that tissues including organs are exposed to air due to incision in surgery, and these tissues can be dehydrated and oxidized leading to their damages. The dehydration and oxidation of tissue including organs during surgery lead to their damages, which are considered as a cause of problems including postoperative tissue adhesion and delay of cure.

Since adhesion especially often inhibits normal movement of tissues including organs, it is considered as one of serious complications after surgery. For instance, the adhesion occurred during tendon surgery may cause dyskinesia. In addition, the organ adhesion after intra-abdominal surgery may cause complications such as ileus, pain and sterility, and sometimes can cause problems such that next surgery becomes very difficult.

Examples of current treatment for prevention of tissue adhesion after surgery and delay of cure include treatment in which saline solution is regularly perfused to exposed organs during surgery and treatment in which tissues such as organs are covered with gauze soaked with saline solution.

However, problems has raised such that in case of perfusion of saline solution, it is difficult to maintain a sufficient covering condition of organs with fluid layer of saline solution preventing from exposure milieu that can cause oxidative stress, and in case of cover with gauze soaked with saline solution, the gauze may interfere surgery operations. It was difficult to maintain conditions in which whole surface of exposed tissue including organs can be blocked from air during surgery.

Therefore, to solve these problems, adhesion preventives composed of chitin, adhesion preventives composed with bridged hyaluronic acid and drugs for prevention of delay of cure have been proposed (for instance, refer to Patent documents 1 and 2).
[Patent Document 1]
Patent Publication No. 2948254
[Patent Document 2]
Patent Publication No. 3420851

However, the previous drugs described above lacked operationality such as user-friendliness, because their component having adhesion preventive function is macromolecule and their forms are mainly film that is placed on intended section or viscous fluid that is applied on intended section. Among substances having effect of adhesion prevention or prevention of cure delay, the ones that are water-soluble and can easily cover the intended section have not been known. While, trehalose ($C_{12}H_{22}O_{11}$), one of saccharides that has been recently used in various field such as foods or cosmetics, has been confirmed to have very high hydrating properties compared with other saccharides. In addition, since trehalose has a similar structure to the cluster structure of $H_2O$, when administered to cell surface, it is considered to persist as glass (amorphous) condition after dehydration, stabilizing cells or proteins instead of $H_2O$ and inhibiting these degenerations.

Trehalose, having such a high performance, is expected to be used for unknown effective indications, and a novel indication for trehalose has been researched in various way. For instance, drugs containing trehalose administered to a mucous membrane (such as Patent document 3), nutrient solutions containing trehalose as a saccharide calorie (such as Patent documents 4 and 5), solutions for transplanted organ containing trehalose (such as Patent document 6), intraocular perfusion/washing agents, eye drops, eye ointments that contain trehalose and have cornea protection properties (such as Patent document 7), association-forming agents between trehalose and unsaturated compounds used for inhibition of chemical changes of unsaturated compounds (such as Patent document 8), inhibitors of lipolysis degradation containing trehalose (such as Patent document 9) have been proposed.
[Patent Document 3]
Kokai (unexamined patent publication) No. 6-256219
[Patent Document 4]
Kokai (unexamined patent publication) No. 6-72883
[Patent Document 5]
Kokai (unexamined patent publication) No. 6-319486
[Patent Document 6]
Kokai (unexamined patent publication) No. 6-40801
[Patent Document 7]
Kokai (unexamined patent publication) No. 9-235233
[Patent Document 8]
Saikohyo No. 2002-24832
[Patent Document 9]
International Publication WO 2004/076602 brochure However, the fact that by applying protection solution using trehalose administered to tissues exposed to air including wounds and organs due to incision in operations such as surgeries, adhesion of wounds and tissue as well as delay of cure will be prevented has not been known yet.

DESCRIPTION OF THE INVENTION

Problems to be Solved by the Invention

The objective of the invention is to provide a solution for tissue adhesion prevention and a method for tissue adhesion prevention that are applicable to general surgery and in which covering condition during surgery is stable and convenient. Other objective of the invention is to provide a novel solution for tissue adhesion prevention and a novel method for tissue adhesion prevention using trehalose.

Means for Solving the Problem

Selecting trehalose and making every effort to realize the objectives described above, we found that when water solution of trehalose is sprayed on surface of animal organs during surgery, postoperative adhesion is prevented and that survival period of cells is prolonged even when the surface is dehydrated after spraying water solution of trehalose.

Furthermore, we found that after spraying solution composed of trehalose and glycosyl-L-ascorbic acid and then dehydrating, surprisingly, both function was synergistically exerted and stronger protection effect compared with use of trehalose alone was shown.

Therefore, the invention is based on the discovery of novel effect of trehalose, and solves the problems described above by composing a solution for tissue adhesion prevention composed of solution of which active ingredient is trehalose. And protection property of tissue is further improved when the solution for tissue adhesion prevention includes glycosyl-L-ascorbic acid.

Uses such that to protect tissues including wounds and organs exposed to air during surgery from damages by each of trehalose and glycosyl-L-ascorbic acid alone or by mixing thereof have not been known yet and the invention is the first solution of these problem.

According to claim 1 of the invention, it is characterized by being the solution for tissue adhesion prevention of which active ingredient is trehalose.

By composing in such way, application of the solution for tissue adhesion prevention prevents dehydration of tissues including wounds and organs exposed to air during surgery as well as inhibits oxidative stress leading to prevention of lipid peroxidation and lipid degradation, and even when wound and tissues are exposed to air during surgery, trehalose forms chelate with metals such as Fe and deactivates metal ion that would cause production of free radicals and therefore inhibits production of free radicals, leading to prevention of tissue adhesion after surgery and delay of wound cure.

In this case, it is suitable that the solution for tissue adhesion prevention includes at least one or more among antioxidants, chelates, antiseptics, hemostatics, anti-inflammatory agents, and polysaccharides, mucopolysaccharides, salt of polysaccharides and salt of mucopolysaccharides having lubricating properties.

By composing in such way, when it includes antioxidants, the tissue protection property of trehalose and the free radical removal property of antioxidants are synergistically exerted to further prevent and inhibit of dehydration and oxidative stress of tissues including wounds and organs during surgery and to reduce production of free radicals. When it includes chelates, it becomes possible to metabolize by conjugating divalent Fe ion with chelates, and to further reduce production of free radicals.

As a result, it becomes possible to prevent more effectively tissue adhesion after surgery and delay of wound cure.

When it includes at least one or more among antiseptics, hemostatics and anti-inflammatory agents, it can be used such as antiseptics, hemostatics and anti-inflammatory agents during surgery or treatment of wounds, the solution for tissue adhesion prevention of the invention is composed such that it already includes at least one or more among antiseptics, hemostatics and anti-inflammatory agents, it is convenient not being necessary to administer separately drugs such as antiseptics, hemostatics and anti-inflammatory agents.

When it includes at least one or more among polysaccharides, mucopolysaccharides, salt of polysaccharides, salt of mucopolysaccharides having lubricating properties, application of this solution for tissue adhesion prevention to tissues including wounds and organs during surgery, it becomes possible to prevent not only dehydration due to exposure to air, oxidative stress, production of free radicals, but also mechanical damages such as microinjury during surgery.

It is well known that microinjury on organs often develops by touching with hands organs during surgery. In this invention, high-molecule having high biocompatibility and lubricating properties is composed, it is able to reduce damages due to touch with surgical gloves or surgical devices and to reduce of mechanical damages of tissues including organs.

In this case, it is suitable that the antioxidant described above is derivative of ascorbic acid.

By composing in such way, the tissue protection property of trehalose and the free radical removal property of derivative of ascorbic acid are synergistically exerted to further prevent and inhibit of dehydration and oxidative stress of tissues including wounds and organs during surgery and to reduce production of free radicals.

As a result, it becomes possible to prevent more effectively tissue adhesion after surgery and delay of wound cure.

In addition, it is suitable that viscosity of the solution for tissue adhesion prevention is adjusted by thickeners.

By composing in such way, when the solution for tissue adhesion prevention is administered to surface of tissues including wounds and organs, membranes covering wounds and tissues become thicker, ensuring the covering of wounds and tissues with sufficient thickness.

In addition, it is suitable that the osmolarity of the solution is adjusted by at least one or more among isotonic electrolyte solutions, plasma expanders, extracellular replacement fluids, maintenance fluids or water.

By composing in such way, the solution for tissue adhesion prevention of the invention can be isotonically adjusted and it becomes possible to give the nutrients of these components to applied tissues of the solution for tissue adhesion prevention.

It is suitable when the solution for tissue adhesion prevention described above is provided as a form of perfusion fluid, spray fluid, solution for spray or vaporization administration, foam-like aerosol preparation, injection solution for intravenous fluids, intravenous fluid.

When the solution for tissue adhesion prevention is provided as a perfusion fluid, it is able to inhibit or prevent impairments of various tissues including adhesion by perfusing during or after surgery with the perfusion fluid of the invention.

In addition, when the solution for tissue adhesion prevention is provided as a spray fluid, it is able to deliver widely and uniformly the solution for tissue adhesion prevention to intended site during surgery as well as to cover the intended site where impairment would be prevented with a sufficient thickness of the solution. Compared with conventional arts in which viscous solution with active ingredient of high-molecular agents is applied or film-form agent is placed on the intended site, the solution of the invention is able to prevent damages of tissue and adhesion of tissues after surgery with a fair degree of certainty by ensuring covering of the intended sites.

Furthermore, when the solution for tissue adhesion prevention described above is provided as a solution for spray or vaporization administration, the solution for tissue adhesion prevention can be sprayed to the intended sites as a mist, and it become possible to deliver widely and uniformly the solution as a refined mist during surgery as well as to cover the intended site where impairment would be prevented with a sufficient thickness of the solution. Compared with conventional arts in which viscous solution with active ingredient of high-molecular agents is applied or film-form agent is placed on the intended site, the solution of the invention is able to prevent damages of tissue and adhesion of tissues after surgery with a fair degree of certainty by ensuring covering of the intended sites. When the solution for tissue adhesion prevention described above is provided as a foam-like aerosol preparation, it is able to deliver widely and uniformly the solution for tissue adhesion prevention to intended site during surgery as well as to cover the intended site where impairment would be prevented with a sufficient thickness of the solution. Compared with conventional arts in which viscous solution with active ingredient of high-molecular agents is applied or film-form agent is placed on the intended site, the solution of the invention is able to prevent damages of tissue and adhesion of tissues after surgery with a fair degree of certainty by ensuring covering of the intended sites.

When the solution for tissue adhesion prevention described above is provided as a injection solution for intravenous fluids or intravenous fluid, it becomes possible to administer the solution for tissue adhesion prevention by means including intravenous administration during at least one or more processes among before, during and after surgery, and also to prevent or inhibit delay of cure after surgery by means including intravenous administration.

Also, the invention is characterized by being a method for tissue adhesion prevention by applying any solution for tissue adhesion prevention described above to local tissue.

By composing the solution for tissue adhesion prevention such that it is applied to local tissue, it is possible to prevent adhesion of applied local tissue or delay of cure.

Advantageous Effect of the Invention

According to the invention, it is characterized by being the solution for tissue adhesion prevention of which active ingredient is trehalose.

By composing in such way, application of the solution for tissue adhesion prevention prevents dehydration of tissues including wounds and organs exposed to air during surgery as well as inhibits oxidative stress leading to prevention of lipid peroxidation and lipid degradation, and even when wound and tissues are exposed to air during surgery, trehalose forms chelate with metals such as Fe and deactivates metal ion that would cause production of free radicals and therefore inhibits production of free radicals, leading to prevention of tissue adhesion after surgery and delay of wound cure.

In addition, since the solution for tissue adhesion prevention contains derivatives of ascorbic acid, the tissue protection property of trehalose and the free radical removal property of derivative of ascorbic acid are synergistically exerted to further prevent and inhibit of dehydration and oxidative stress of tissues including wounds and organs during surgery and to reduce production of free radicals. As a result, it becomes possible to prevent more effectively tissue adhesion after surgery and delay of wound cure.

BEST MODE FOR CARRYING-OUT OF THE INVENTION

Figure 1:
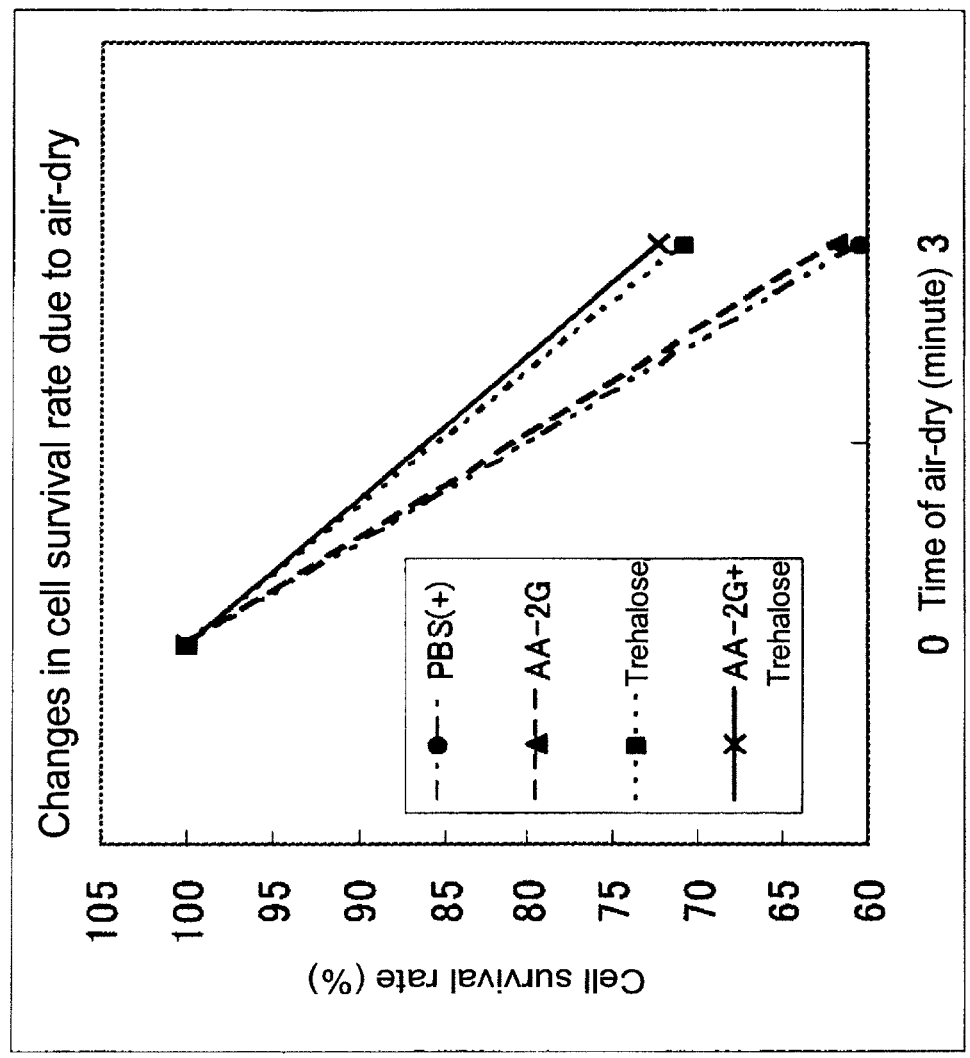
FIG. 1 It is a graph showing changes in cell survival rate due to air-dry in Example 1 of the invention.

The solution for tissue adhesion prevention of the invention is a solution for tissue adhesion prevention of which active ingredient is trehalose. It is administered directly to tissues including wounds and organs during surgery. It relates to the one used as adhesion preventives that prevent tissue adhesion after surgery or therapeutic agents that prevent delay of wound cure.

In this specification, hereinafter, "wound" referred to injury, "tissue" to body's tissue such as skin, organ, muscle, nerve, cartilage, bone.

The solution for tissue adhesion prevention of the invention can be applied to various animals, especially it is suitably used in mammalian species, especially in humans.

Hereinafter, we describe one example of the invention in detail. Note that the composition described hereinafter does not limit the invention, but can be adapted within the scope of the invention.

This example relates to the solution for tissue adhesion prevention and the one used as tissue-covering agent or adhesion preventive that prevent adhesion of tissue after surgery and delay of wound cure, and as therapeutic agent that enhance cure of tissue and wounds after surgery. The solution for tissue adhesion prevention of this example is a solution of which the active ingredient is trehalose.

The solution for tissue adhesion prevention of this example is administered to tissue surface being exposed during surgery. There is no special limitation due to surgical site or professional field, it can be widely used in not only laparotomy or thoracotomy but also neurosurgical procedures, orthopedic procedures relating to tendon or ligament, hepatic surgery, gynecologic procedures etc.

The tissues exposed during surgery include, for instance, except wounds occurred by surgical incision and organs exposed by incision, muscle, nerve, cartilage, bone. Also, it is applicable for bone marrow exposed by orthopedic osteotomy. Furthermore, it has been reported that trehalose inhibits development of nerve degenerative disorders in mice, therefore, it is applicable for cranial nerves and peripheral nerves exposed by neurosurgical procedures.

Trehalose is a non-reducing disaccharide that two molecules of glucose bind by 1 to 1 binding.

Trehalose is a publicly known substance isolated from rye in 1832 for the first time. It widely presents in the free state in nature including animals, vegetables and microorganisms. It is contained for rich amount in yeasts such as bakers' yeast and brewers' yeast, and it is a saccharide often observed in foods. Also, it is a saccharide relates to various organisms, and it is said that because trehalose is present, insects such as Macrobiotus and Brachionus and vegetables such as *Selaginella tamariscina* can survive in rigorous condition such as desert.

In this example, any of hydrated crystal trehalose, anhydrous crystal trehalose, carbohydrate solution containing trehalose, alpha, alpha-trehalose (in the narrow sense), alpha, beta-trehalose (neo-trehalose), beta, beta-trehalose (iso-trehalose) can be used, however, it is suitable when hydrated crystal trehalose or anhydrous crystal trehalose composed of especially alpha, alpha-trehalose (alpha-D-glucopyranosyl-alpha-D-glucopyranoside) is used. In addition, only if it is the trehalose described above, any one produced from natural trehalose, starch, maltooligosaccharides, glucoses can be used.

In addition, to compose a solution for tissue adhesion prevention of which the active ingredient is trehalose, derivatives that produce trehalose in vivo after administration can be used instead of trehalose.

As solvent for dissolution of trehalose, isotonic electrolyte fluids, plasma expanders or maintenance fluids or water can be used.

The isotonic electrolyte fluids refer to electrolyte preparations that are isotonic. The isotonic fluids refer to intravenous fluid that is isotonic, that is, of which the osmolarity is similar with body fluid. As isotonic electrolyte fluid, for instance, extracellular replacement fluid can be used.

The extracellular replacement fluid refers to intravenous isotonic electrolyte fluid used for replacement or adjustment of extracellular fluid in case of depletion of extracellular fluid due to problems such as hemorrhage, diarrhea, and dehydration. As extracellular replacement fluid, for instance, physiological saline solution (0.9% saline solution), Ringer's acetate, Ringer's lactate can be used.

Plasma expanders also refers to plasma extenders being used as intravenous fluid when proteins such as albumin in plasma are lost due to problems such as hemorrhage for its substitute, and contains high-molecular component such as dextran, starch, recombinant albumin. As plasma expander, dextran 40 preparation, dextran 70 preparation, hydroxyethyl starch (HES) preparation, modified gelatin preparation can be used. Maintenance fluid is an intravenous fluid being used for replacement and maintenance of water/electrolyte when oral intake is impossible or insufficient. As maintenance fluid, starting fluid, maintenance fluid, and high-concentration glucose added maintenance fluid can be used.

Water acts as solvent for dissolution of trehalose. As water, for instance, pure water or distilled water can be used. It is suitable for use of sterile distilled water.

The concentration of trehalose in the solution for tissue adhesion prevention is suitable when it is more than 10 mM, preferably within 50 to 350 mM.

When it is less than 10 mM, the cell protection effect can not be expected. Also, when it is more than 350 mM, it became hypertonic.

To the solution for tissue adhesion prevention, at least one or more among group including antiseptics, hemostatics and anti-inflammatory agents may be added.

As antiseptics, for instance, publicly known antiseptics such as povidone-iodine, potassium peroxomonosulfate, dimethyldidecyl ammonium chloride, as hemostatics, for instance, publicly known hemostatics such as thrombin, sodium alginate, as anti-inflammatory agents, for instance, non-steroid anti-inflammatory drugs are used.

Furthermore, to the solution for tissue adhesion prevention, antioxidants may be added.

As antioxidant, for instance, water-soluble stable vitamin C can be used. The water-soluble stable vitamin C include derivatives of ascorbic acid classified into pro-vitamin C agents such as glycosyl-L-ascorbic acid (hereinafter refer as AA-2G) and ascorbic acid-2-phosphoric acid (AA-2P).

AA-2G also refers as ascorbic acid-2-glucoside that presents in nature and is degraded in vivo by alpha-glucosidase into L-ascorbic acid and D-glucose, developing similar physiological activity to L-ascorbic acid. AA-2G, even in high concentration, does not have cell toxicity and its promoting effect of collagen synthesis and promoting effect of cell proliferation and differentiation are significant, which lead to its frequent use not only in food or cosmetic field but also culture of connective tissues such as fibroblasts.

As AA-2G, a series of 2-glucopyranosyl-L-ascorbic acid including 2-O-alpha-D-monoglucopyranosyl-L-ascorbic acid composed by glycosidic linkage of L-ascorbic acid at C-2 position and one or more D-glucose is suitable for use. Also, AA-2G is not limited to glycosyl-L-ascorbic acid as organic acid, and can be any of physiologically acceptable mineral salts and salts of organic acid such as sodium salt, potassium salt, calcium salt, magnesium salt and ammonium salt that liberate glycosyl-L-ascorbic acid in aqueous media.

The concentration of AA-2G in the solution for tissue adhesion prevention is suitable to be more than 0.01 mM, preferably within 0.1 to 200 mM. When it is less than 0.01 mM, the cell protection effect can not be expected.

As antioxidant, minerals such as vitamin C, vitamin E, selenium, in vivo antioxidant enzyme such as SOD (super oxide dismutase), catalase, glutathione peroxidase, vegetable-derived antioxidants (SOD-like substances) that contain carotenoids that are lipid-soluble pigment of vegetables such as alpha-carotine, beta-carotine, gamma-carotine lycopene, xanthophyll, and polyphenols that are contained in flower, leaf, bark, stem such as flavonoid, catechin, tannin, anthocyanin, isoflavon, quercetin, phycocyanobilin, phycoerythrobilin can be used.

To the solution for tissue adhesion prevention, furthermore, chelates may be added.

As chelates, DMPS (dimercaptopropanolsulfonate), DMSA (dimercaptosuccinate), ALA (alpha-lipoic acid), EDTA (ethylenediaminetetraaceticacid), L-glutamicdiacetic acid/tetrasodium (GLDA/4Na), sodium gluconate can be used. Since chelates can be metabolized by conjugating divalent Fe ions, it becomes possible to prevent the newly production of free radical caused by Fe ions, leading to further more effective prevention of adhesion of tissues including organs after surgery and delay of wound cure.

To the solution for tissue adhesion prevention, furthermore, at least one of polysaccharides, mucopolysaccharides and the salts thereof and ones having lubricating properties may be added.

As polysaccharides and the salts thereof, for instance, polysaccharides containing carboxyl group or the water-soluble salts thereof or polysaccharides containing carboxyl group bridged by ion bonding or the water-soluble salts thereof can be used. As polysaccharides containing carboxyl group, carboxymethylcellulose, carboxymethylchitin, carboxymethylchitosan, carboxymethylstarch, alginic acid, pectin, carboxymethyldextran etc. can be used. Mucopolysaccharides include, except for hyaluronic acid (HA), heparin, heparin sulfate, and chondroitin sulfate.

As water-soluble salt, sodium salts, alkali metal salts or alkali earth metal salts can be used.

In addition, it is suitable for use of hyaluronic acid among polysaccharides, mucopolysaccharides and the salts thereof. Especially, mucopolysaccharides such as hyaluronic acid are known to have force to gelate water of hundreds to thousands of its amount and to give water retentivity, viscosity, lubricity to body fluid. If it is added to the solution for tissue adhesion prevention of this example, when covering surface of tissues such as wounds and organs with the solution for tissue adhesion prevention, it is able to give lubricity to the cover layer and to obtain preventive effect of mechanical damages to wounds and tissues.

The solution for tissue adhesion prevention of this example is adjusted such that its osmolarity is within 200 to 450 Osm and its pH is within 7 to 8 after mixing the substances described above.

The reason why the osmolarity is adjusted within 200 to 450 Osm is to adapt the osmolarity of human body. In addition, the reason why the pH is within 7 to 8 is to prevent acidolysis of tissue cells of wounds or organs administered with the solution for tissue adhesion prevention.

For adjustment of osmolarity, colloid osmotic pressure adjustment agents such as hydroxyethylstarch, dextranstarch are used. The osmolarity is adjusted low considering the condensation due to dehydration during surgery.

Also, the solution for tissue adhesion prevention of this example is adjusted such that the temperature during use would be near body temperature, that is, 35 to 38 degrees C. By this procedure, when the solution for tissue adhesion prevention is administered during surgery, the intended sites of tissues such as wounds and organs would not be cooled and it is able to prevent cooling during surgery that causes postoperative pain.

The solution for tissue adhesion prevention of this example can be administered anytime only before cure of wounds progresses, although it is preferable to administer during surgery or immediately before suture of wounds. Also it can be administered continuously during surgery.

In addition, the solution for tissue adhesion prevention of this example is administered directly to tissue surface including wounds and organs exposed to air by incision during surgery. As method of administration, after the solution for tissue adhesion prevention is impregnated with carriers such as gauze or non-woven fabric, they may cover the tissue surface including wounds and organs. However, it is more suitable if the solution is poured directly to tissue surface including wounds and organs, or after composing the solution for tissue adhesion prevention of this example as spraying solution, it is sprayed with spraying devices.

By composing the solution for tissue adhesion prevention as spraying solution to be able to spray it to the intended sites, the solution that works as the solution for tissue adhesion prevention of wounds can be sprayed widely and uniformly to the intended sites as wall as the intended site where impairment would be prevented can be covered with a sufficient thickness of the solution.

As spraying devices, both spray with two fluid nozzles in which solution drops are carried with air or carbon dioxide and spray with one fluid nozzle in which solution becomes tiny particles by pressure can be used.

The one fluid nozzle does not use gas for providing drops. Therefore, use of the one fluid nozzle prevents dehydration or oxidation of the tissues including wounds and organs or lowering temperature by heat of evaporation. So, it is preferable from the aspect of prevention of damages of wounds and tissues. The one fluid nozzle includes hollow cone nozzle and full cone nozzle in which the solution is sprayed out in cone shape by rotational flow, nozzle of which angle of spraying cone can be changed, flat nozzle in which the drops sprayed out in plane shape, solid nozzle in which the drops go straight forward, particle spray in which the drops become tiny particles that are all applicable.

On the other hand, when amount of polysaccharides, mucopolysaccharides and the salts thereof is increased to improve preventive effect of mechanical damages of tissues including wounds and organs during surgery, it is recommended to use spray with two fluid nozzles because the viscosity of the solution for tissue adhesion prevention becomes higher. When the solution for tissue adhesion prevention is poured directly to tissue surface including wounds and organs, a certain viscosity is needed, therefore, the viscosity should be adjusted using thickeners such as gums including mucopolysaccharides or heteropolysaccharides, synthesized organic high-molecular composition including polyvinylalchol or polyacrylic acid, cellulose derivatives, starch derivatives.

Also, it is suitable that the solution for tissue adhesion prevention of this example is composed as solution for spray or vaporization administration, and this solution for spray or vaporization administration is administered by spraying the mist atomized with devices such as nebulizer and vaporizer. By composing the solution for tissue adhesion prevention as solution for spray or vaporization administration to spray it to the intended sites in atomized mist state, the solution that works as the solution for tissue adhesion prevention can be sprayed widely and uniformly to the intended sites as wall as the intended site where impairment would be prevented can be covered with a sufficient thickness of the solution.

As nebulizer and vaporizer, any of ultrasonic ones in which it is atomized by shaking with ultrasonic oscillator, dropping ones in which drops are carried with gas, jet injection ones in which the solution becomes tiny particles under pressure can be used.

For instance, a device provided heater, ultrasonic oscillator, air blasting fan, spray orifice in which the solution for spray or vaporization administration heated with heater to given temperature is atomized by shaking with ultrasonic oscillator, and the mist obtained by atomizing is sprayed from spray orifice with air blasting fan can be used. Also a two-phase vaporizer with the solution for tissue adhesion prevention composed of 2 solutions, that is, water and concentrated solution of the solution for tissue adhesion prevention, provided water tank with heater and concentrated solution tank with ultrasonic oscillator can be used. When the two-phase vaporizer is used, steam produced by heating with heater and mist of concentrated solution atomized with ultrasonic oscillator are met in pathway, and the mist of the solution for tissue adhesion prevention produced by the meeting is sprayed out from spray orifice.

Also, by composing the solution for tissue adhesion prevention of this example as foam-like aerosol preparation, and this foam-like preparation can be administered using heater, pressure device, aerosol device provided nozzle. The foam-like aerosol preparation is composed by adding publicly known surfactants to the solution for tissue adhesion prevention already described.

By the way, in endoscopic surgery widely used recent years, the problems of complications due to dehydration and oxidation of tissues including organs during surgery have been occurred. By applying the solution for tissue adhesion prevention and the method for tissue adhesion prevention of this example, it is possible to prevent complications after endoscopic surgery. That is, using spray device with one fluid nozzle fixed to the top of extension tube, the spray solution composed of the solution for tissue adhesion prevention of this example can be sprayed to the tissues including organs involved in the surgery during or after endoscopic surgery. In addition, it is suitable if the extension tube of one fluid nozzle and cable of endoscopic device are fixed each other, operation of spray device is facilitated because the materials inserted into body during endoscopic procedure are unified.

Furthermore, the solution for tissue adhesion prevention of this example can be composed as perfusion fluid, intravenous fluid, injection solution for intravenous fluids.

The perfusion fluid is composed as a water solution dissolved trehalose and AA-2G in publicly known intravenous fluid such as saline solution and Ringer's solution, and provided packed into intravenous fluid bag. The perfusion fluid is used by substituting and perfusing operation field during or after surgery.

Intravenous fluid preparations are prepared by dissolving trehalose with publicly known tonicity agents such as sodium chloride, glycerin and publicly known buffer fluid such as phosphate and acetate in publicly known solvents such as saline solution and Ringer's solution, and provided packed into intravenous fluid bag. The intravenous fluid preparations are used in at least one or more processes among before, during and after surgery using means such as intravenous drip.

Injection solution for intravenous fluids are prepared by dissolving trehalose and AA-2G with publicly known tonicity agents such as sodium chloride, glycerin and publicly known buffer fluid such as phosphate and acetate in publicly known solvents such as saline solution and Ringer's solution.

This injection solution is used as mixed solution with publicly known intravenous fluid such as glucose injection, xylitol injection, saline solution, dextran 40 injection, amino acid injection, Ringer's solution.

The injection solutions are used in at least one or more processes among before, during and after surgery using means such as intravenous drip by injecting into intravenous fluid.

It has been found that during surgery, when tissues such as organs and wounds are exposed to oxygen in air, dehydration, oxidative stress and free radicals occur leading to oxidative impairments such as membrane phospholipids impairment, protein impairment and DNA damages.

In this example, by administer the solution for tissue adhesion prevention of this example directly on tissues including organs and wounds during surgery, trehalose prevents dehydration of tissues and wounds and also prevents oxidative impairments due to oxidative stress during surgery. Also, trehalose forms chelates with metals such as Fe, deactivates metal ions that cause free radicals, inhibits production of free radicals. By preventing dehydration, oxidative impairments due to oxidative stress and production of free radicals, it becomes possible to prevent adhesion and delay of cure caused by oxidative impairments after surgery. In addition, since the solution for tissue adhesion prevention of this example contains AA-2G that is antioxidant by adding radicals, it provides a synergistic effect such that wounds and exposed tissues can be protect more efficiently by combination of trehalose and AA-2G that have different mechanisms of action.

EXAMPLE

Hereinafter, we describe a specific example of the invention in detail. The following examples are to describe the invention and do not limit the invention to themselves.

Example 1

As cells, HepG2 cells (human hepatoma-derived cell lines) were used.

For all reagents other than HepG2 cells, AA-2G, trehalose, DMEM media, FCS, neutral red, reagent grade chemicals were used. In addition, as sample solution in which HepG2 cells were activated, 4 kinds of solution; PBS (+) solution, 2.5 mM AA-2G solution, 132 mM trehalose solution, 2.5 mM AA-2G+132 mM trehalose mixed solution were prepared.

A reagent ascorbic acid-2-glucoside (AA2G; Hayashihara Biochemical Labs., Inc.) was dissolved in distilled water to obtain 2.5 mM AA-2G solution. And a highly purified hydrated crystal trehalose in powder (Reagent trehalose; Hayashihara Biochemical Labs., Inc.) was dissolved in distilled water to obtain 132 mM trehalose solution. The reagents ascorbic acid-2-glucoside and the highly purified hydrated crystal trehalose in powder were dissolved in distilled water to obtain 2.5 mM AA-2G+132 mM trehalose mixed solution. Then, pH and osmolarity of these 4 kinds of sample solutions were adjusted. Adjustment of osmolarity of 2.5 mM AA-2G solution, 132 mM trehalose solution, 2.5 mM AA-2G+132 mM trehalose mixed solution was performed by adjusting with sodium chloride of PBS (+) to be isotonic.

The pH and osmolarity of each sample after adjustment were as follows; pH 7.2 and 279 mOsm for PBS (+) solution, pH 6.8 and 265 mOsm for 2.5 mM AA-2G solution, pH 7.2 and 283 mOsm for 132 mM trehalose solution and pH 7.0 and 282 mOsm for 2.5 mM AA-2G+132 mM trehalose mixed solution.

Then, HepG2 cells were seeded with $4\times10^4$ cells/well each to four 12-well plates, and incubated in DMEM media (Nissui Pharmaceutical Co., Ltd) containing 10% FCS (Gibco) for 4 days. Then the DMEM media containing 10% FCS were replaced with 4 kinds of sample solutions; PBS (+) solution, 2.5 mM AA-2G solution, 132 mM trehalose solution, 2.5 mM AA-2G+132 mM trehalose mixed solution, and activated at 37 degrees C. for 1 hour.

Two control plates and two test plates were prepared for cells activated with 4 kinds of sample solutions, respectively. For each two test plates, one plate was air-dried for 5 minutes and other plate was air-dried for 3 minutes. The two control plates were not air-dried.

Then, cells of each plate was replaced with no serum DMEM media and incubated at 37 degrees C. for 1 hour. After replacing with 0.02% neutral red (Wako Pure Chemical Industries, Ltd, hereinafter referred to NR), they were activated at 37 degrees C. for 40 minutes. After removal of NR solution and addition of PBS (+), they were left to stand at 37 degrees C. for 40 minutes, PBS (+) was removed and they were air-dried for 5 minutes. They were added NR extracts and left to stand at 37 degrees C. for 10 minutes, then each sample was distributed over 96-well plate and the absorbance at the wavelength of 570 nm was measured.

The absorbance of the control plates to which air-dry was not performed was considered as cell survival rate of 100%, and the cell survival rate of the test plates to which air-dry was performed for 3 minutes was calculated. The results are shown in the graph indicating changes in cell survival rate by air-dry in FIG. 1.

That is, the cell survival rates in test plates to which air-dry were performed for 3 minutes were 60.4%, 61.8%, 70.7% and 72.3% for PBS (+) solution, 2.5 mM AA-2G solution, 132 mM trehalose solution and 2.5 mM AA-2G+132 mM trehalose mixed solution, respectively.

Also, the cell survival rates of the test plate to which air-dry was performed for 5 minutes for PBS (+) solution was 54.9%. As mentioned above, the cell protection effect was calculated for each sample solution considering the cell survival rate of the control plate as 100%, the cell protection effect was not observed for 2.5 mM AA-2G solution, and the cell protection effect was observed for 132 mM trehalose solution and 2.5 mM AA-2G+132 mM trehalose mixed solution when the plates were air-dried for 3 minutes.

Therefore, the cell protection effect from air-dry of these reagents is considered to be effective for slight dehydration of approximately 3 minutes.

Figure 2:
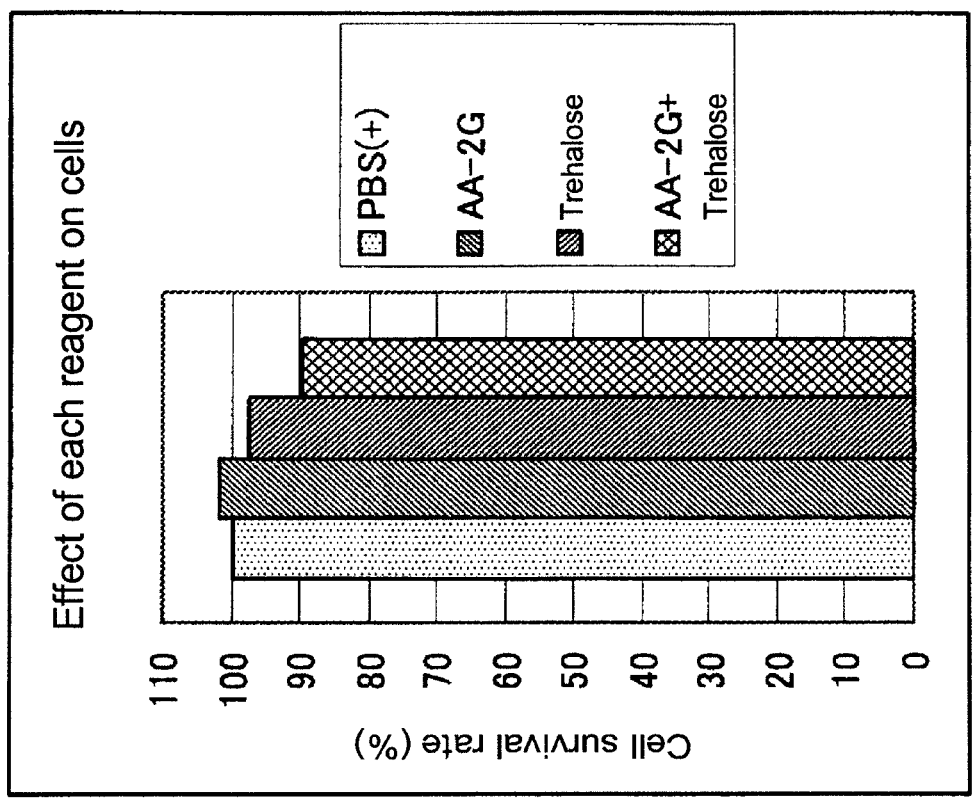
FIG. 2 It is a graph showing effect of each reagent on cell in Example 1 of the invention.

Also, the cell survival rates of control plates for each sample solution to which air-dry was not performed were calculated. The results are shown in the graph indicating the effect of each reagent on cells in FIG. 2.

That is, the cell survival rates in control plates, when the cell survival rate of control plate for PBS (+) was considered to be 100%, were 101.6%, 97.6% and 89.6% for 2.5 mM AA-2G solution, 132 mM trehalose solution and 2.5 mM AA-2G+132 mM trehalose mixed solution, respectively.

Also, when the cell survival rate of control plate for PBS (+) was considered to be 100%, the effects on cells of 2.5 mM AA-2G solution, 132 mM trehalose solution and 2.5 mM AA-2G+132 mM trehalose mixed solution were calculated. Each cell survival rate was 101.5%, 97.7% and 89.7%, respectively, and it was found that adjustment of pH and osmolarity alleviated the effects on cells.

Since protection mechanism of cells from dehydration and oxidation is known to be similar with the protection mechanism of body's tissue from dehydration and oxidation, the water solution containing trehalose and antioxidant as active ingredient was confirmed to act as a solution for tissue adhesion prevention by this Example 1.

Example 2

In this example, abdominal adhesion model was prepared using rabbits by desiccating surface of intestines during abdominal surgery, and the preventive effect of intestine adhesion by trehalose was discussed.

As trehalose, powder trehalose (Reagent trehalose; Hayashihara Biochemical Labs., Inc.) and $^+$NaCl were dissolved in sterile distilled water of 250 mL as 2%; solution, sterilized by filtration with filter (Millex; Millpore Co., Bedford) and poured to sterile container and stored at room temperature. As test animals, five female New Zealand White rabbits weighing 2.85 to 3.2 kg aged of 14 weeks (Std:NZW, Japan SLC, Inc., Shizuoka) were used. The rabbits were kept in animal laboratory (room temperature of 24+/−1 degrees C., humidity of 30 to 700) in The University of Tokyo, Graduate School of Agricultural and Life Sciences Veterinary Medical Center. The rabbits were acclimatized for 1 week after purchase, and during this period blood test (complete blood count, BUN, Cre, ALT, ALP) and general x-ray test were performed to confirm that abnormality was not present. The experiment of this example was performed according to the Manual of animal experiment of University of Tokyo.

The experiment of this example was performed as follows.

As anesthesia, 5 mg/kg of ketamine (KETALAL 50; Sankyo Lifetech Co., Ltd., Tokyo) and 0.1 mg/kg of medetomidine (DOMITOL; Meiji Seiyaku Co., Ltd., Tokyo) were intramuscularly injected as preoperative medication, and after intubation maintained with isoflurane (ISOFLU; Dainippon Pharmaceutical Co., Ltd., Osaka). Before operation, 10 mg/kg of enrofloxacin (BAYTRIL; Bayer Medical Ltd., Tokyo) was subcutaneously administered as antibiotics, and during operation 10 mL/kg/hr of lactated Ringer's solution (FUSO; Fuso Pharmaceutical Industries, Ltd., Osaka) was intravenously administered, After operation, single dose of 20 μg/kg of buprenorphine (LEPETAN; Otsuka Pharmaceutical Co., Ltd., Tokyo) as analgesics was subcutaneously administered. During anesthesia, ECG, $ETCO_2$ and $SpO_2$ were monitored and maintained within their normal variations.

Three rabbits among the five rabbits were randomized to the control group, and the other two rabbits were classified into the trehalose group. For the five rabbits, after disinfection of operative field, abdominal median incision was performed and intestines were exposed as far as possible and serum was wiped with gauze. For control group (three rabbits) they were left desiccated and for trehalose group (two rabbits) whole intestines were sprayed with trehalose for several times. During this period, ovariohysterectomy was performed according to given method. The time period of laparotomy was 30 to 60 minutes for both groups. The 3-0 monofilament nylon fiber (Bear surgical suture; Bear Medic Corporation, Chiba) was used for ovariohysterectomy and closure of abdominal wall, and the 4-0 monofilament polyglyconate fiber (MAXON; Syneture Co., Ltd., Connecticut) was used for subcutaneous tissues and stapler (Manipler AZ-35W; Mani Inc., Tochigi) was used for skin suture. After operation, general condition and wounds were observed and they were killed by overdose of pentobarbital after 2 weeks. The adhesion status in peritoneal cavity was macroscopically observed and recorded as well as tissues of adhesion sites were removed as pathohistological test material and fixed in formalin.

The clinical findings after 2 weeks and the macroscopic findings of adhesion status after laparotomy of each case are shown in Table 1.

TABLE 1

Clinical findings after 2 weeks and macroscopic findings after laparotomy

| Rabbit no. | Clinical findings | Findings after laparotomy Adhesion sites in intestines | Adhesion of stump of uterus |
|---|---|---|---|
| Control group | | | |
| 1. | No abnormal findings | 3 sites of adhesion | Present |
| 2. | No abnormal findings | 5 sites of adhesion | Present |
| 3. | Subcutaneous seroma | Not less than 5 sites of adhesion | Present |
| Trehalose group | | | |
| 1. | Partial dehiscence of skin suture | 2 sites of adhesion (Suspected) | Present |
| 2. | No abnormal findings | No significant adhesion sites | Present |

No clinical abnormality was observed in all cases at 2 weeks after operation. However, moderate subcutaneous retention of serum just under surgical wound in 1 case in control group. The result of bacterial cultures of this serum was negative. In addition, a part of skin suture site was removed and showed ulcer in 1 case in trehalose group.

For adhesion, a significant adhesion with surrounding tissue at suture of uterus stumps by ovariohysterectomy was observed in all cases in both groups. For adhesion of intestines, multiple adhesions (more than 3 sites) of mild to moderate degree were confirmed in all 3 rabbits of control group. In trehalose group, 2 sites of mild adhesion were suspected in 1 rabbit, however, they can be considered as normal bond of intestines. In remaining 1 rabbit, no significant adhesion was macroscopically observed.

This Example shows that spray of trehalose would be effective for prevention of abdominal adhesion due to desiccation. Trehalose has high hydrating properties, and trehalose in amorphous state is considered to prevent adhesion by covering serous membrane of intestines and stabilizing cells.

Example 3

In this example, abdominal adhesion model was prepared using rabbits by desiccating surface of intestines during abdominal surgery, and the preventive effect on intestine adhesion by trehalose was discussed.

As trehalose, powder trehalose (Reagent trehalose; Hayashihara Biochemical Labs., Inc.) were dissolved in sterile distilled water of 250 mL as 7% solution, sterilized by filtration with filter (Millex; Millpore Co., Bed ford) and poured to sterile container and stored at room temperature.

As test animals, 20 female New Zealand White rabbits weighing 2.6 to 3.2 kg aged of 14 weeks (Std:NZW, Japan SLC, Inc., Shizuoka) were used. The rabbits were kept in animal laboratory (room temperature of 24+/−1 degrees C., humidity of 30 to 70%) in The University of Tokyo, Graduate School of Agricultural and Life Sciences Veterinary Medical Center. The rabbits were acclimatized for 1 week after purchase, and during this period blood test (complete blood count, BUN, Cre, ALT, ALP) and general x-ray test were performed to confirm that abnormality was not present. The experiment of this example was performed according to the Manual of animal experiment of The University of Tokyo.

The experiment of this example was performed as follows.

As anesthesia, 5 mg/kg of ketamine (KETALAL 50; Sankyo Lifetech Co., Ltd., Tokyo) and 0.1 mg/kg of medetomidine (DOMITOL; Meiji Seiyaku Ca, Ltd., Tokyo) were intramuscularly injected as preoperative medication, and after intubation maintained with isoflurane (SOFLU Dainippon Pharmaceutical Co., Ltd., Osaka). Before operation, 10 mg/kg of enrofloxacin (BAYTRIL; Bayer Medical Ltd., Tokyo) was subcutaneously administered as antibiotics, and during operation 10 mL/kg/hr of lactated Ringer's solution (FUSO; Fuso Pharmaceutical Industries, Ltd., Osaka) was intravenously administered. After operation, single dose of 20 μg/kg of buprenorphine (LEPETAN; Otsuka Pharmaceutical Co., Ltd., Tokyo) as analgesics was subcutaneously administered.

During anesthesia, ECG, $ETCO_2$ and $SpO_2$ were monitored and maintained within their normal variations.

Connecticut), the 3-0 mono filament polyglyconate suture (MAXON; Syneture CO., Ltd., Connecticut) was used for closure of abdominal wall, and the 4-0 mono filament polyglyconate suture (MAXON; Syneture Co., Ltd., Connecticut) was used for subcutaneous tissues and stapler (ManiplerAZ-35W; Mani Inc., Tochigi) was used for skin suture.

Ten rabbits among the twenty rabbits were randomized to the control group, and the other ten rabbits were classified into the trehalose group.

The control group (10 rabbits) was left desiccated. The time period of laparotomy was 60 minutes.

For the trehalose group, trehalose solution was sprayed over the whole abdominal cavities every 15 minutes (0 minutes, 15 minutes, 30 minutes, 45 minutes, 60 minutes after starting the operation). The time period of laparotomy was 60 minutes. After operation, general condition and wounds were observed and rabbits were euthanized by excessive administration of pentobarbital two weeks after the operations.

The adhesion status in peritoneal cavity was macroscopically observed and recorded as well as tissues of adhesion sites were removed as pathohistological test materials and fixed in formalin. The clinical findings after 2 weeks and the macroscopic findings of adhesion status after laparotomy of each case are shown in Table 2.

TABLE 2

The clinical findings after 2 weeks and the macroscopic findings of adhesion status after laparotomy

| | | The control group | | | | | | | | | | The trehalose group | | | | | | | | | |
|---|---|---|---|---|---|---|---|---|---|---|---|---|---|---|---|---|---|---|---|---|
| Rabbits No. | | 1 | 2 | 3 | 4 | 5 | 6 | 7 | 8 | 9 | 10 | 1 | 2 | 3 | 4 | 5 | 6 | 7 | 8 | 9 | 10 |
| Adhesion sites | jejunum - abdominal wall | ++ | − | − | − | − | − | − | − | − | − | − | − | − | − | − | − | − | − | − | − |
| | cecum - colon | − | − | − | − | − | − | − | − | − | − | + | − | − | − | − | − | − | − | − | − |
| | greater omentum - rectum | − | − | − | − | − | − | ++ | − | − | − | − | − | − | − | − | − | − | − | − | − |
| | greater omentum - stomach | ++ | − | − | − | − | − | − | − | − | − | − | − | − | − | − | − | − | − | − | − |
| | greater omentum - small intestine | − | − | − | − | − | − | ++ | − | − | ++ | − | − | − | − | − | − | − | − | − | − |
| | small intestine - rectum | − | − | − | − | − | − | − | − | − | − | − | − | − | − | ++ | − | − | − | − | − |
| | abdominal wall - bladder | − | ++ | − | − | − | − | − | − | − | − | − | − | − | − | − | − | − | − | − | − |
| | abdominal wall - fat | − | + | − | + | − | − | − | − | − | − | − | − | − | − | − | − | − | − | − | − |
| | colon-fat | − | − | − | − | − | − | ++ | − | − | − | − | − | − | − | − | − | − | − | − | − |
| Score-Total | | 4 | 3 | 0 | 1 | 0 | 0 | 4 | 2 | 0 | 2 | 1 | 0 | 0 | 0 | 2 | 0 | 0 | 0 | 0 | 0 |

"non-adhesion: −"
"Adhesions of mild degree (abruption enabled): +"
"Adhesions of severe degree (abruption enabled): ++"

For the 20 rabbits, after disinfection of operative field, abdominal median incision was performed and intestines were exposed as far as possible and serum was wiped with gauze. Total ovariohysterectomy performed according to given method. Four section of ovarion arteries and veins were severed after being ligated with 4-0 mono filament polyglyconate suture (MAXON; Syneture Co., Ltd., Connecticut). Also, uterovaginal stump were sutured with 5-0 mono filament polyglyconate suture (MAXON; Syneture Co., Ltd., No clinical abnormality was observed in all cases at 2 weeks after operation.

For adhesion, obvious adhesions with surrounding organ tissues at suture of uterovaginal stumps, which are surgical sites of ovariohysterectomy, and vascular ligations were observed in all cases in control group. For adhesion between abdominal organs of at desiccated intestine surfaces. Adhesions of mild and severe degree were confirmed in 6 of 10 control cases and 2 of 10 in trehalose cases. For adhesion scores between organs, trehalose group achieved at +3, whereas +16 in control group. The prevention ratio was 81% (Wilcoxon rank-sum test: at p<0.05).

This Example shows that trehalose can obviously prevent and reduce adhesions and would be effective for abdominal adhesion due to desiccation.

Trehalose has high hydrating properties, and is considered to prevent adhesion by covering serous membrane of intestines and stabilizing cells.

Because solution spray made it possible to diffuse and penetrate over serous membranes organ, whole organs could be covered by trehalose.

The invention claimed is:

1. The method for tissue adhesion prevention, comprising:
   locally applying a solution comprising alpha, alpha-trehalose to living tissues exposed to air during surgery, wherein the solution for tissue adhesion prevention comprises alpha, alpha-trehalose in an amount effective to provide a cell membrane phospholipid-protecting effect and to prevent tissue adhesion following the surgery.

2. The method for tissue adhesion prevention according to claim 1, wherein said solution for tissue adhesion prevention further comprises at least one selected from the group consisting of an antioxidant, a chelate, an antiseptic, a hemostatic, an anti-inflammatory agent, a polysaccharide, a mucopolysaccharide, a salt of a polysaccharide, and a salt of a mucopolysaccharide having a lubricating property.

3. The method for tissue adhesion prevention according to claim 2, wherein said antioxidant is a derivative of ascorbic acid.

4. The method for tissue adhesion prevention according to claim 1, wherein a viscosity of the solution for tissue adhesion prevention is adjusted by a thickener.

5. The method for tissue adhesion prevention according to claim 1, wherein an osmolarity of the solution for tissue adhesion prevention is adjusted by at least one selected from the group consisting of an isotonic electrolyte fluid, a plasma expander, an extracellular replacement fluid, a maintenance fluid, and water.

6. The method for tissue adhesion prevention according to claim 1, wherein a viscosity of the solution for tissue adhesion prevention is adjusted by a thickener and an osmolarity of the solution for tissue adhesion prevention is adjusted by at least one selected from the group consisting of an isotonic electrolyte fluid, a plasma expander, an extracellular replacement fluid, a maintenance fluid, and water.

7. The method for tissue adhesion prevention according to claim 1, wherein said solution for tissue adhesion prevention is in a form of a perfusion fluid, a spray fluid, a solution for spray or vaporization administration, an aerosol preparation, an injection solution for intravenous fluids, or an intravenous fluid.

8. The method for tissue adhesion prevention according to claim 1, wherein a viscosity of the solution for tissue adhesion prevention is adjusted by a thickener and the solution for tissue adhesion prevention is in a form of a perfusion fluid, a spray fluid, a solution for spray or vaporization administration, an aerosol preparation, an injection solution for intravenous fluids, or an intravenous fluid.

9. The method for tissue adhesion prevention according to claim 1, wherein an osmolarity of the solution for tissue adhesion prevention is adjusted by at least one selected from the group consisting of an isotonic electrolyte fluid, a plasma expander, an extracellular replacement fluid, a maintenance fluid, and water, and the solution for tissue adhesion prevention is in a form of a perfusion fluid, a spray fluid, a solution for spray or vaporization administration, an aerosol preparation, an injection solution for intravenous fluids, or an intravenous fluid.

10. The method for tissue adhesion prevention according to claim 1, wherein a viscosity of the solution for tissue adhesion prevention is adjusted by a thickener, and an osmolarity of the solution for tissue adhesion prevention is adjusted by at least one selected from the group consisting of an isotonic electrolyte fluid, a plasma expander, an extracellular replacement fluid, a maintenance fluid, and water, and the solution for tissue adhesion prevention is in a form of a perfusion fluid, a spray fluid, a solution for spray or vaporization administration, an aerosol preparation, an injection solution for intravenous fluids, or an intravenous fluid.

11. The method for tissue adhesion prevention according to claim 2, wherein a viscosity of the solution for tissue adhesion prevention is adjusted by a thickener.

12. The method for tissue adhesion prevention according to claim 3, wherein a viscosity of the solution for tissue adhesion prevention is adjusted by a thickener.

13. The method for tissue adhesion prevention according to claim 2, wherein an osmolarity of the solution for tissue adhesion prevention is adjusted by at least one selected from an isotonic electrolyte fluid, a plasma expander, an extracellular replacement fluid, a maintenance fluid, or water.

14. The method for tissue adhesion prevention according to claim 3, wherein an osmolarity of the solution for tissue adhesion prevention is adjusted by at least one selected from an isotonic electrolyte fluid, a plasma expander, an extracellular replacement fluid, a maintenance fluid, or water.

15. The method for tissue adhesion prevention according to claim 2, wherein a viscosity of the solution for tissue adhesion prevention is adjusted by a thickener and an osmolarity of the solution for tissue adhesion prevention is adjusted by at least one selected from an isotonic electrolyte fluid, a plasma expander, an extracellular replacement fluid, a maintenance fluid, or water.

16. The method for tissue adhesion prevention according to claim 3, wherein a viscosity of the solution for tissue adhesion prevention is adjusted by a thickener and an osmolarity of the solution for tissue adhesion prevention is adjusted by at least one selected from an isotonic electrolyte fluid, a plasma expander, an extracellular replacement fluid, a maintenance fluid, or water.

17. The method for tissue adhesion prevention according to claim 2, wherein said solution for tissue adhesion prevention is a form of a perfusion fluid, a spray fluid, a solution for spray or vaporization administration, an aerosol preparation, an injection solution for intravenous fluids, or an intravenous fluid.

18. The method for tissue adhesion prevention according to claim 2, wherein a viscosity of the solution for tissue adhesion prevention is adjusted by a thickener and the solution for tissue adhesion prevention is in a form of a perfusion fluid, a spray fluid, a solution for spray or vaporization administration, an aerosol preparation, an injection solution for intravenous fluids, or an intravenous fluid.

19. The method for tissue adhesion prevention according to claim 2, wherein an osmolarity of the solution for tissue adhesion prevention is adjusted by at least one selected from an isotonic electrolyte fluid, a plasma expander, an extracellular replacement fluid, a maintenance fluid, or water, and the solution for tissue adhesion prevention is in a form of a perfusion fluid, a spray fluid, a solution for spray or vaporization administration, an aerosol preparation, an injection solution for intravenous fluids, or an intravenous fluid.

20. The method for tissue adhesion prevention according to claim 2, wherein a viscosity of the solution for tissue adhesion prevention is adjusted by a thickener, and an osmolarity of the solution for tissue adhesion prevention is adjusted by at least one selected from an isotonic electrolyte fluid, a plasma expander, an extracellular replacement fluid, a maintenance fluid, or water, and the solution for tissue adhesion prevention is in a form of a perfusion fluid, a spray fluid, a solution for spray or vaporization administration, an aerosol preparation, an injection solution for intravenous fluids, or an intravenous fluid.

21. The method for tissue adhesion prevention according to claim 1, wherein the surgery is chosen from laparotomy, thoracotomy, neurosurgery, orthopedic surgery, hepatic surgery, and gynecologic surgery.

* * * * *